United States Patent [19]
Thurkauf et al.

[11] Patent Number: 6,121,260
[45] Date of Patent: Sep. 19, 2000

[54] METHOD OF TREATING CONDITIONS SUSCEPTIBLE TO MODULATION OF NPY RECEPTORS WITH DIARYLIMIDAZOLE DERIVATIVES

[75] Inventors: Andrew Thurkauf, Danbury; Jun Yuan, Guilford; Alan Hutchison, Madison; Charles A. Blum, Westbrook; Richard L. Elliot, East Lyme; Marlys Hammond, Salem, all of Conn.

[73] Assignees: Neurogen Corporation, Branford, Conn.; Pfizer Inc., New York, N.Y.

[21] Appl. No.: 09/109,558

[22] Filed: Jul. 2, 1998

Related U.S. Application Data

[60] Provisional application No. 60/051,711, Jul. 3, 1997.

[51] Int. Cl.$^7$ .............. A61K 31/54; A61K 31/541; A61K 31/5415; A61K 31/5377; A61K 31/538; A61K 31/4166

[52] U.S. Cl. .................. 514/228.2; 514/230.5; 514/235.8; 514/396; 514/397; 514/398; 514/399; 514/400; 544/58.5; 544/62; 544/105; 544/139; 548/311.7; 548/336.5; 548/341.5; 548/343.1; 548/343.5

[58] Field of Search .............. 548/343.5, 343.1, 548/341.5, 336.5, 311.7; 514/396, 399, 398, 397, 235.8, 228.2, 230.5, 400; 544/139, 105

[56] References Cited

U.S. PATENT DOCUMENTS

| | | | |
|---|---|---|---|
| 3,297,710 | 1/1967 | Silversmith | 548/343.5 |
| 3,657,441 | 4/1972 | Jensen et al. | 548/343.5 X |
| 4,134,983 | 1/1979 | Baldwin | 548/343.5 X |
| 4,665,023 | 5/1987 | Deneke et al. | 435/28 |
| 4,757,124 | 7/1988 | Koyanagi et al. | 526/62 |
| 4,758,639 | 7/1988 | Koynagi et al. | 526/62 |
| 4,853,383 | 8/1989 | Baldwin et al. | 514/335.8 |
| 5,017,467 | 5/1991 | Masukawa et al. | 430/558 |
| 5,292,669 | 3/1994 | Guder et al. | 435/18 |
| 5,296,609 | 3/1994 | McCort et al. | 548/325.1 |
| 5,498,301 | 3/1996 | Hirao et al. | 148/269 |
| 5,620,999 | 4/1997 | Weier et al. | 514/398 |

FOREIGN PATENT DOCUMENTS

| | | |
|---|---|---|
| 0257897 | 3/1988 | European Pat. Off. . |
| 0353606 | 2/1990 | European Pat. Off. . |
| 0448765 | 10/1991 | European Pat. Off. . |
| 2113861 | 6/1972 | France . |
| 42-1546 | 1/1967 | Japan . |
| 1051076 | 10/1983 | U.S.S.R. . |
| 9720823 | 6/1997 | WIPO . |

OTHER PUBLICATIONS

Lombardino, Joseph G., et al. "Preparation and Antiinflammatory Activity of Some Nonacidic Trisubstituted Imidazoles." Journal of Medicinal Chemistry, vol. 17, No. 11 (1974, pp. 1182–1188 XP–002080630.

Suzuki, Mamoru et al. "Syntheses of 2–Aryl–4–(3–thienyl)imidazole Derivatives with Antiinflammatory Properties." Chemical and Pharmaceutical Bulletin, vol. 34, No. 8 (1986) pp. 3111–3120 XP–002080631.

Baldwin, J. J., et al. "β–Adrenergic Blocking Agents with Acute Antihypertensive Activity." Journal of Medicinal Chemistry, vol. 22, No. 6 (1979) pp. 687–694 XP002080632.

*Primary Examiner*—Floyd D. Higel
*Attorney, Agent, or Firm*—Ladas & Parry

[57] ABSTRACT

Certain diaryl imidazoles act as partial agonists or antagonists for NPY receptors, in particular NPY 5 receptors. They are of use, for example in treating loss of appetite. Such compounds bear aryl groups in the 2 position. Many of the compounds are novel.

43 Claims, No Drawings

METHOD OF TREATING CONDITIONS SUSCEPTIBLE TO MODULATION OF NPY RECEPTORS WITH DIARYLIMIDAZOLE DERIVATIVES

RELATED APPLICATION

This application claims priority from provisional application 60/051,711 filed on Jul. 3, 1997.

BACKGROUND OF THE INVENTION

1. Field of the Invention

This invention relates to pharmaceutical compositions containing certain diarylimidazole derivatives which selectively bind to human NPY receptors. Some of such diarylimidazoles are believed to be novel. The invention further relates to the use of such compounds in treating feeding disorders such as obesity and bulimia as well as certain cardiovascular diseases such as essential hypertension.

2. Prior Art

Neuropeptides known as Neuropeptide Y (NPY) are believed to have a role in a variety of functions in the body and in particular have been associated with stimulation of appetite but also to effect anxiolysis and regulation of coronary tone. Such compounds bind to a number of different receptor sites. U.S. Pat. No. 5,571,695 (Selbie et al.) describes the genomic DNA sequences that code for the Y-1 receptor. U.S. Pat. No. 5,554,621 (Poindexter et al.) describes certain 4-phenyl dihydropyridines that are NPY antagonists and noted the existence of at least five receptor subtypes for NPY. U.S. Pat. No. 5,545,549 (Gerald et al) describes the human Y2 receptor and the DNA coding for it. U.S. Pat. No. 5,516,653 (Bard et al.) describes the human Y4 receptor and the DNA coding for it. U.S. Pat. No. 5,602,024 (Gerald et al) describes the human Y5 receptor and the DNA coding for it. It states that this receptor seems to be the most significant for appetite stimulation.

Many diarylimidazoles are known for a variety of uses. For example, European Patent Publication 627499 (Shikoku Chemicals Corporation) and its United States equivalent, U.S. Pat. No. 5,498,301 (Hirao) describe the use of 2,4-diphenylimidazole and 2,4-diphenyl-5-methyl imidazoles as water based surface treating agents for use on copper surfaces and compares their activity to that of 2,4,5-triphenylimidazole. The 2-phenyl group may be substituted by alkyl or halo groups and the 4-phenyl group by alkyl, halo, alkoxy, di-loweralkylamino, cyano or nitro groups. Specific compounds mentioned in the United States Patent include 2-phenyl-4-(4-chlorophenyl)imidazole, 2-phenyl-4-(2,4-dichlorophenyl)imidazole, 2-phenyl-4-(4-bromophenyl)imidazole, 2-phenyl-4-(2-tolyl)imidazole, 2-phenyl-4-xylylimidazole, 2-(4-chlorophenyl)-4-phenylimidazole, 2-(4-bromophenyl)-4-phenylimidazole, 2-(2,4-dichlorophenyl)-4-phenylimidazole, 2-(4-tolyl)-4-phenylimidazole, 2-(4-methoxyphenyl)-4-phenylimidazole, 2-(4-dimethylaminophenyl)-4-phenylimidazole, 2-(4-cyanophenyl)-4-phenylimidazole, 2-(3-nitrophenyl)-4-phenylimidazole, 2-(2,4-xylyl)-4-phenylimidazole, 2-(4-chlorophenyl)-4-(4-chlorophenyl)imidazole, 2-(2,4-dichlorophenyl)-4-(2-tolyl)imidazole, 2-(2-bromophenyl)-4-(2,3-xylyl)imidazole, 2-(4-ethyl phenyl)-4-(2-chlorophenyl)imidazole, 2-(2-ethoxyphenyl)-4-(4-bromophenyl)imidazole, 2-(2-cyanophenyl)-4(4-tolyl)imidazole, 2-(3-nitrophenyl)-4-(2,3-dichlorophenyl)imidazole, 2-(4-diethylaminophenyl)-4-(4-flurophenyl)imidazole, 2-(4-chlorophenyl)-4-phenyl-5-methylimidazole, 2-(4-tolyl)-4-phenyl-5-methylimidazole, 2-(2,4-dichlorophenyl)-4-phenyl-5-methylimidazole, 2-(2,3-xylyl)-4-phenyl-5-methylimidazole, 2-(4-methoxyphenyl)-4-phenyl-5-methylimidazole, 2-(4-dimethylaminophenyl)-4-phenyl-5-methylimidazole, 2-(2-nitrophenyl)-4-phenyl-5-methylimidazole, 2-(3-cyanophenyl)-4-(4-chlorophenyl)-5-methylimidazole, 2-(2-nitrophenyl)-4-phenyl-5-methylimidazole, 2-(3-cyanophenyl)-4-(4-chlorophenyl)-5-methylimidazole.

PCT Publication WO 95/04274 (Nippon Soda Co. Ltd.) describes the use of a wide range of imidazoles for pest control including 2-(optionally halogenated)phenyl-4-(optionally halogenated) phenylimidazoles.

Suzuki et al. in Chem. Pharm. Bull (1986) 34, 3111–20 describe the synthesis of 2-aryl-4-(3-thienyl)imidazole derivatives of use as antiinflamatory agents.

U.S. Pat. No. 5,017,467 describes 2,4-di(2-substituted aminophenyl) imidazoles wherein the 5 position is optionally substituted by a group capable of being split off by reaction with an oxidized product of a color developing agent for use as a cyan coupler in photography.

East German patent publication 299059 (Chemical Abstracts 117:131199) describes 2-(2-hydroxyphenyl)-4-substituted imidazoles wherein the substituent in the 4 position may be an optionally substituted phenyl group and the 5 position may be substituted by a phenyl or alkyl group.

East German patent publication 297816 (Chemical Abstracts 116:214504) describes 2-arylimidazole compounds wherein the 4 or 5 positions may have aryl substituents of use as lipoxygenase inhibitors.

German Patent Publication 3917677 (Chemical Abstracts 115:25542) describes 2-(4-hydroxy-3,5-di-tert.-butyl) phenyl-4-(4-dialkylamino)phenylimidazoles of use as chromogenic substrates in analytical redox reactions. The 4-phenyl group and the 5 position of the imidazole ring may be further substituted by alkyl groups.

German Patent Publication 3411997 (Chemical Abstracts 104:145136) describes compounds of use as redox indicators including 2-(substituted phenyl)-4-(substituted phenyl) imidazoles.

Soviet Patent Publication 1051076 (Chemical Abstracts 101:90924) describes 2-phenyl-4-(phenyl or p-tolyl) imidazoles which may be methyl- or phenyl-substituted in the 5 position.

European Patent Publication 0131973 (Instituto de Angeli S. p. A.) describes the use of certain aryl imidazoles, including 2-phenyl-4-(4-nitro-phenyl)-1H-imidazole and 2-phenyl-4-(4-amino-phenyl)-1-imidazole as intermediates in the production of amidines useful as $H_2$ receptor blocking agents.

U.S. Pat. Nos. 4,757,124 and 4,758,639 (Koyangi et al ) describe the use of inter alia 2,4-diphenylimidazole for prevention of scaling of the walls of a polymerization vessel used in the production of vinyl polymers.

Other compounds found in the course of database searches include: 4-(2,4-dichlorophenyl)-2-phenyl-5-methylimidazole; 2,4-bis-(2,4-dichlorophenyl)-imidazole (C.A. Registry No 197514-18-4); 2-(4-methoxyphenyl)-2-(2-aminophenyl) imidazole (C.A. Registry No 197011-25-9); 2-(4-methoxyphenyl)-2-(2-trifluoromethylphenyl) imidazole (C.A. Registry No 174356-09-3); 4-(2-ethylaminophenyl)-2-phenylimidazole (C.A. Registry 170448-20-1); N-[2-(2-phenyl-1H-imidazol-yl)-phenyl] acetamide (C.A. Registry 162706-94-7); 2-(4-chlorophenyl)-2-(3-trifluoromethylphenyl)imidazole (C.A. Registry 162701-76-0); N-[4-[2-(2-hydroxyphenyl)-1H- imidazol-yl]phenyl]acetamide (C. A. Registry 138500-29-5) and its methoxy homolog (C. A. Registry 138500-28-4); several 2-phenylimidazoles wherein the 4 position is substituted by a 3,3-dimethyl-2H-indole-2-one group (C. A. Registry Nos 135466-37-4, 135466-36-3; 135437-73-9; 135437-72-8; 135437-71-7; 135437-68-2; 135437-66-0; 135437-65-9; 135437-64-8; 135437-63-7; 135437-62-6; 135437-61-5; 135437-60-4 and 135437-59-1); analogous 2(1H)-3,4-dihydroquinolones (C.A. Registry Nos 135437-70-6 and 135437-67-1), 2,4-bis-(2-aminophenyl)-imidazole (C.A. Registry No 131623-81-9); 4-(4-hydroxyphenyl)-2-phenylimidazole (C.A. Registry No 111273-30-4); 2,4-bis (4-phenoxyphenyl)imidazole (C.A. Registry 107783-02-8); 2,4-bis(bi-phenyl-4-yl)imidazole (C.A. Registry 106304-01-2); 4-(2-phenyl-1H-imidazol-4-yl)benzeneamine (C.A. Registry No.96139-68-3); various 2-(2-hydroxyphenyl) 4-(possibly substituted) phenylimidazoles having methyl, ethyl, butyl or phenyl substituents in the 5-position; and a number of more complicated structures.

SUMMARY OF THE INVENTION

This invention provides pharmaceutical compositions comprising compounds of Formula I which interact with Neuropeptide Y receptors and in particular with NPY5 receptors and methods of treatment of conditions susceptible to such interactions. It further relates to the use of such compounds in treating feeding disorders such as obesity and bulima as well as certain cardiovascular diseases such as essential hypertension. Suitable compounds are those of Formula I:

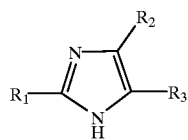

where $R_1$ is an unsubstituted or mono, di or trisubstituted aryl group wherein said aryl group is mono or bicyclic, in which case only the ring bound to the imidazole group ring need be aromatic, and said aryl group may be carbocyclic or contain up to 2 hetero atoms which may be nitrogen, oxygen or sulfur, and said substituents are selected from the group consisting of halogen, trihalomethyl, cyano, hydroxy, straight or branched chain lower alkyl having 1–6 carbon atoms, straight or branched chain lower alkoxy having 1–6 carbon atoms (which alkyl or alkoxy groups themselves may be substituted by an amino or mono- or di- alkyl amino group or an acyl group), straight or branched chain lower thioalkoxy having 1–6 carbon atoms, acyloxy groups, amino, amino mono or disubstituted with straight or branched chain lower alkyl having 1–6 carbon atoms, said alkyl groups being optionally substituted with a hydroxy or amino group, mono or disubstituted carbamyl where the CO group is bound to the aryl group and wherein the substituents are lower alkyl or aryl lower alkyl, mono or di-alkyl carbamates having up to 6 carbon atoms in each alkyl group or mono or diaryl carbamates or any 2 adjacent substituents on the aryl ring may be represented as $X(CH_2)_nY(CH_2)_mZ$ where X, Y and Z are either a direct bond, oxygen, sulfur, or NR where R is hydrogen or lower alkyl and n and m are 1, 2 or 3.

One of $R_2$ and $R_3$ is selected from the group consisting of hydrogen, hydroxymethyl, alkoxymethyl having up to 6 carbon atoms in each alkoxy group, straight or branched chain lower alkyl having 1–6 carbon atoms, cyano, or a carboxylic or carboxylate ester group wherein the esterifying group typically contains up to six carbon atoms.

The other of $R_2$ and $R_3$ is an aryl group which is either unsubstituted or mono, di or trisubstituted wherein said aryl groups are mono or bicyclic (in which case only the ring bound to the imidazole grouping need be aromatic) and may be carbocyclic or contain up to 2 hetero atoms and said substituents are selected from the group consisting of halogen, trihalomethyl, cyano, hydroxy, straight or branched chain lower alkyl having 1–6 carbon atoms, straight or branched chain lower alkoxy having 1–6 carbon atoms (which alkyl or alkoxy groups themselves may be substituted by amino or a mono- or di- alkyl amino groupor an acyl group), straight or branched chain lower thioalkoxy having 1–6 carbon atoms, acyloxy groups, amino, amino mono or disubstituted with straight or branched chain lower alkyl having 1–6 carbon atoms (said alkyl groups being optionally substituted with a hydroxy or amino group), mono- or disubstituted carbamyl where the CO group is bound to the alkyl group and the substituents are lower alkyl or aryl lower alkyl, mono- or di-alkyl carbamates having up to 6 carbon atoms in each alkyl group or mono or diaryl carbamates additionally any two adjacent substituents on the aryl ring may be represented as $—X—(CH_2)_n—Y(CH_2)_mZ$ where X, Y and Z are either a direct bond, oxygen, sulfur, or NR where R is hydrogen or lower alkyl and n and m are 1, 2 or 3.

These compounds are selective partial agonists or antagonists at human NPY5 receptors and are useful in the diagnosis and treatment in mammals of feeding disorders such as obesity and bulimia as well as certain cardiovascular diseases such as essential hypertension and congestive heart failure.

DETAILED DESCRIPTION OF THE INVENTION

The compounds of use in the present invention can be described by general Formula:

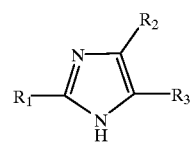

where $R_1$ is an aryl group, which may be unsubstituted or mono, di or trisubstituted. The aryl groups from which $R_1$ may be selected are typically mono or bicyclic groups, in which case only the ring bound to the imidazole group need be aromatic, and may be carbocyclic or heterocyclic containing up to 4 hetero atoms but no more than 2 hetero atoms in each ring. Typically each ring of the aryl group is a five or six membered ring. Suitable aryl groups include phenyl, naphthyl, indanyl, pyrrolyl, furanyl, thienyl, pyridyl, pyrimidinyl, indolyl, benzofuranyl, thianaphthyl, isoindolyl, isobenzofuranyl, quinolinyl, isoquinolinyl, quinazolinyl, indazolyl, quinoxalinyl, cinnolinyl 1,2,3,4-tetrahydroquinolinyl, 2,3-dihydroindolyl, phenomorpholinyl, benzodioxazinyl, phenothiomorpholinyl and methylenedioxyphenyl groups. Suitable substituents include: halogen, trihalomethyl, cyano, hydroxy, straight or branched chain lower alkyl having 1–6 carbon atoms, straight or branched chain lower alkoxy having 1–6 carbon atoms, which alkyl and alkoxy groups themselves may be substituted by an amino or a mono- or di-alkylamino group or a mono- or di-alkaryl group such as benzyl or by an acyl group, straight or branched chain lower thioalkoxy having 1–6 carbon atoms, acyloxy groups such as alkanoyloxy groups of from 2 to 7 carbon atoms, such as acetoxy, and aroyloxy groups such as benzoyloxy, amino, amino mono or disubstituted with straight or branched chain lower alkyl having 1–6 carbon atoms, said alkyl groups being optionally substituted with a hydroxy or amino group, mono or disubstituted carbamyl groups wherein the substituent is lower alkyl or aryl lower alkyl, mono or disubstituted carbamyl where the CO group is bound to the aryl ring and the substituents are lower alkyl or aryl lower alkyl, carbamates such as mono- or di-alkyl carbamates having up to 6 carbon atoms in each alkyl group or mono or diaryl carbamates such as methyl phenyl carbamate and diphenyl carbamate. In addition any two adjacent substituents may be represented as —X—$(CH_2)_n$—Y—$(CH_2)_m$—Z— where X, Y and Z are either a direct bond, oxygen, sulfur, or NR where R is hydrogen of lower alkyl and n and m are 1,2 or 3.

One of $R_2$ and $R_3$ is selected from hydrogen, hydroxymethyl, alkoxy-methyl having from 1 to 6 carbon atoms in the alkyl group, straight or branched chain lower alkyl having 1–6 carbon atoms, cyano, or a carboxylic or carboxylate ester group wherein the esterifying group typically has up to six carbon atoms.

The other of $R_2$ and $R_3$ is an aryl group either unsubstituted or mono, di or trisubstituted. Suitable aryl groups are mono or bicyclic and may be carbocyclic or contain up to 2 hetero atoms. They include phenyl, naphthyl, indanyl pyrrolyl, furanyl, thienyl, pyridyl, pyrimidinyl, indolyl, benzofuranyl, thianaphthenyl, isoindolyl, isoberzofuranyl, quinolinyl, isoquinolinyl quiazolinyl, indazoyle, quinoxalinyl, cinnolinyl, 1,2,3,4-tetrahydroquinolinyl, 2,3-dihydroindolyl, phenomorpholinyl, benzodioxazinyl, phenothiomorpholinyl and methylenedioxyphenyl groups. Suitable substituents include: halogen, trihalomethyl, cyano, hydroxy, straight or branched chain lower alkyl having 1–6 carbon atoms, straight or branched chain lower alkoxy having 1–6 carbon atoms, (which alkyl or alkoxy groups may be substituted with an amino or a mono- or dialkyl amino group or a mono- or di-alkaryl amino group or an acyl group), straight or branched chain lower thioalkoxy having 1–6 carbon atoms, acyl groups such as acetyl, acyloxy groups such as alkanoyloxy groups of from 2 to 7 carbon atoms, such as acetoxy, and aroyloxy groups such as benzoyloxy, amino, amino mono or disubstituted with straight or branched chain lower alkyl having 1–6 carbon atoms, said all groups being optionally substituted with a hydroxy or amino group, mono or di substituted carbamyl groups wherein the CO group is bound to the aryl group and the substituents are lower alkyl or aryl lower alkyl, carbamates such as mono- or di-alkyl carbamates having up to 6 carbon atoms in each alkyl group or mono or diaryl carbamates such as methyl phenyl carbamate and diphenyl carbamate. In addition any two adjacent substituents may be represented as —X—$(CH_2)_n$—Y—$(CH_2)_m$—Z— where X Y and Z are either a direct bond, oxygen, sulfur, or NR where R is hydrogen of lower alkyl and n and m are 1, 2 or 3.

When used herein the term "alkyl" includes branched and straight chain alkyl groups and cycloalkyl groups. Such alkyl groups may be interrupted by an oxygen or sulfur atom. "Alkyl" further comprises groups containing both a cyclic and an acyclic portion. In the absence of any indication to the contrary, alkyl groups referred to in this application have from 1 to 8 carbon atoms and any cyclo alkyl group or portion of an alkyl group will have from three to six carbon atoms in the ring and may optionally contain some unsaturation. A "lower alkyl" group is an alkyl group as just defined containing up to six carbon atoms. "Acyl" groups may contain alkyl, aryl or aralkyl groups but normally no more than 8 carbon atoms. The term "alkaryl" is used to denote groups such as benzyl and phenylethyl groups. It will be recognized by those skilled in the art that several of the compounds of use in the present invention may exist in tautomeric form. In such cases, reference to a particular compound encompasses both tautomeric forms.

Particularly useful classes of compounds according to the present invention include those wherein the aryl group of $R_1$ is selected from aryl monocyclic groups which may be carbocyclic or contain up to two hetero atoms (N, O, or S) and is either unsubstituted or is substituted by up to three groups such as halogen, trihalomethyl, cyano, hydroxy, straight or branched chain lower alkyl of 1–6 carbon atoms, straight or branched chain lower alkoxy having 1–6 carbon atoms, straight or branched chain lower thioalkoxy having 1–6 carbon atoms, acyloxy groups, amino, amino mono or disubstituted with straight or branched chain lower alkyl having 1–6 carbon atoms, said alkyl groups being optionally substituted with a hydroxy or amino group, mono or di-alkyl carbamates having up to 6 carbon atoms in each alkyl group or mono or diaryl carbamates. Additionally any 2 adjacent substituents on an aryl ring may be represented as —X, $(CH_2)_n$—Y—$(CH_2)_m$—Z— where X Y and Z are either a direct bond, oxygen, sulfur, or NR where R is hydrogen or lower alkyl and n and m are 1, 2 or 3. For example $R_1$ can most usefully be a phenyl, 4-fluorophenyl, pyridin-2-yl or a thiophene group.

Similarly, particularly useful non-aryl $R_2$ and $R_3$ groups include hydrogen, alkyl (as defined above).

Particularly useful aryl groups for $R_2$ or $R_3$ include as phenyl, thienyl, pyridyl, and napthyl for example bearing up to three substituents selected from halo especially chloro or fluoro), alkoxy (such as methoxy) and alkyl (such as methyl, ethyl groups. Particularly preferred groups include 4-methylphenyl, 3-methoxyphenyl, 4-methoxyphenyl, 3-bromophenyl, 4-bromophenyl, 4-chlorophenyl, 4-fluorophenyl, 3-cyanophenyl, 4-cyanophenyl, 4-methoxy-2-fluorophenyl, 4-ethoxy-2-fluorophenyl, 3-fluoro-4-methoxyphenyl, 2-fluoro-4-methoxyphenyl, 3-acetylphenyl, naphthyl, 1,4-benzodioxan-6-yl and benzo [b] morpholinyl, 4-alkyl (e.g. methyl, ethyl or n-propyl) benzo[b] morpholinyl, 4-alkyl.-2H,-3H,4H-benzo[e]1,4-thiazinyl, 3-methylaminophenyl, 4-dimethylaminophenyl, 3-ethylaminophenyl, 3-(2-methylbutylaminomethyl)phenyl, 3-(ethylbutylaminomethyl)phenyl, 3(1,2-dimethylpropylaminomethyl)phenyl, 3-[(3-cyclohexyl-1-phenylpropyl)methylaminomethyl]phenyl, 3-[(2-cyclohex-1-enylethyl)aminomethy]phenyl, 3-[(3-methylethoxy)propylaminomethyl]phenyl, 3-(tert.-butylaminomethyl) phenyl, 3-[methyl-(1-phenylpropyl) aminomethyl]phenyl, 3-(methylethylaminomethyl)phenyl and 3-[(4-methylphenyl) metylaminomethyl]phenyl.

Non-toxic pharmaceutical salts include salts of acids such as hydrochloric, phosphoric, hydrobromic, sulfuric, sulfinic, formic, toluene sulfonic, hydroiodic, acetic, mesylate and the like. Those skilled in the art will recognize a wide variety of non-toxic pharmaceutically acceptable addition salts.

Many of the compounds of use in the compositions of the present invention are believed to be novel. We are, however, aware of prior disclosures of compounds wherein 1) $R_1$ and whichever of $R_2$ and $R_3$ is aryl are both phenyl, a bromophenyl group, a chlorophenyl group, 2,4-dichlorophenyl, a cyanophenyl group, 2-methoxyphenyl, 3-aminophenyl, 4-aminophenyl, 4-trifluoromethylphenyl, 3-hydroxyphenyl, 4-hydroxyphenyl, 3-acetylaminophenyl, 4-phenoxyphenyl or biphenyl;

2) when $R_1$ is phenyl, whichever of $R_2$ and $R_3$ is aryl is 2-acetylaminophenyl, chlorophenyl, biphenyl, 4-aminophenyl, p-tolyl, xylyl, 4-methoxyphenyl, 4-dimethylaminophenyl, 4-bromophenyl or 4-hydroxy-2,5-di-tert.-butylphenyl, 3) when one of $R_2$ or $R_3$ is phenyl, $R_1$ is 2-hydroxyphenyl, 4-hydroxyphenyl, 4-methoxyphenyl, 2-methylphenyl, 4-chlorophenyl, biphenyl, 2,4-dichlorophenyl, 2,4-xylyl, 4-cyanophenyl or 6-quinolyl; and 4) $R_1$ is 2-hydroxyphenyl when $R_2$ or $R_3$ is p-tolyl, $R_1$ is 4-hydroxy-3-methoxyphenyl when $R_2$ or $R_3$ is 4-dimethylaminophenyl; $R_1$ is 4-hydroxy-3,5-dimethoxyphenyl when $R_2$ or $R_3$ is 4-aminophenyl; $R_1$ is 4-hydroxy-3,5-di-tert.-butylphenyl when $R_2$ or $R_3$ is 4-hydroxyphenyl; $R_1$ is 4-chlorophenyl when $R_2$ or $R_3$ is 3-trifluoromethylphenyl; $R_1$ is 2-hydroxyphenyl when $R_2$ or $R_3$ is 2- or 4-acetamidophenyl; $R_1$ is 2-methoxyphenyl when $R_2$ or $R_3$ is 4-acetamidophenyl; $R_1$ is 2-ethoxyphenyl when $R_2$ or $R_3$ is 2-acetamidophenyl; $R_1$ is 4-methoxyphenyl when $R_2$ or $R_3$ is 2-aminophenyl or 2-trifluorophenyl; $R_1$ is 2-aminophenyl when $R_2$ or $R_3$ is 2-isopropylcarbamylphenyl or 5-acetamido-2-hydroxyphenyl, $R_1$ is 2-cyanophenyl when $R_2$ or $R_3$ is 4-tolyl, $R_1$ is 2-bromohenyl when $R_2$ or $R_3$ is 2,3-xylyl, $R_1$ is 3-cyanophenyl when $R_2$ or $R_3$ is 4-chlorophenyl and $R_1$ is 4-dimethylamino when $R_2$ or $R_3$ is an ester of 3-methoxy 4-hydroxyphenyl or 3,5-dimethoxy4-acetoxyphenyl.

Among the compounds we believe to be novel are diarylimidazoles of the above formula wherein $R_1$ is 4-fluorophenyl, those wherein $R_2$ or $R_3$ is an N-substituted aminomethylphenyl group or is selected from the group consisting of naphthyl, cyanophenyl, N-substituted benzo[b]morpholine, 2H,3H-benzo[e]1,4-dioxin and N-substituted 2H,3H, 4H-benzo[e]1,4-thiazine.

Compounds according to the invention include: 2(4-fluorophenyl)-4-(4-methoxyphenyl)imidazole hydrochloride, 2-(thienyl-2-yl)-4-(4-chlorophenyl)imidazole, 2-(4-fluorophenyl)-4-(4-chlorophenyl)imidazole hydrochloride, 2-phenyl-4-(3-fluoro-4-methoxyphenyl)imidazole hydrochloride.

The pharmaceutical utility of compounds of this invention are indicated by the following assays for human NPY receptor activity.

Assays for Human NPY receptor binding activity

SKNMC Binding Assay

The procedure used is similar to that described by Gordon et al. (J. Neurochem. 55:506–513, 1990). SK-M-MC cells were purchased from ATCC (Rockville, Md.). Cells were maintained at 37° C. and 5% $CO_2$ in Dulbecco's modified essential media (DMEM) with L glutamine and 110 mg/L sodium pyruvate, which was supplemented with 10% fetal bovine serum and 25 mM HEPES (pH 7.3). The binding assay was performed in 24-well plates (Falcon) when the cells were confluent. Taking care to not disturb the cells on the bottom of the wells, the media was aspirated, and 0.5 ml of Dulbecco's phosphate buffered saline (DPBS) with calcium and magnesium were added to each well. The DPBS was aspirated and an additional aliquot of DPBS was added and aspirated. To begin the assay, binding buffer consisting of serum-free DMEM containing 0.5% bovine serum albumin, 0.1% bacitracin and 0.1 mM phenylmethylsulfonylfluoride was added to each well. The cells, the binding buffer, the drug dilution and [$^{125}$I]PYY (MEM-DuPont: 50000–75000 cpm 50 pM) were added to yield a final volume of 250 $\mu$l. Nonspecific binding was defined with 1 $\mu$M NPY (porcine or human, Bachem Calif.). After a 2 hour incubation at room temperature, the plates were then put on ice and the wells were aspirated. The cells were washed twice with 0.5 ml of ice-cold DPBS. A dilute solution of Triton X-100 (1%) was then added to each well. After approximately twenty minutes at room temperature, an aliquot from each well was transferred to a 12×75 mm test tube, and the amount of [$^{125}$I] was quantitated on a gamma counter with an efficiency of 80–85% (Genesys 5000, Laboratory Technologies). $IC_{50}$ values were calculated with the nonlinear curve fitting program RS/1 (SigmaPlot, Jandel).

[$^{125}$I]Binding at Human NPY Receptors Expressed in Sf9 Cells

Baculovirus-infected Sf9 cells expressing recombinant human SPY 5 receptors are harvested at 48 hours. At the time of harvest, cell pellets are resuspended in lysis buffer (20 mM Tris-HCl pH 7.4, 5 mM EDTA, 0.5$\mu$g/ml leupeptin, 2 $\mu$g/ml Aprotonin and 200 HM PMSF) and homogenized using a Polytron (setting 3,25–30 seconds). Homogenates are centrifuged at 4° C. for 5 minutes at 200×g (~1.5 rpm) to pellet the nuclei. The supernatant is collected into a fresh tube and centrifuged at 48,000×g for 10 minutes. Pellets are washed once in lysis buffer and centrifuged. The final pellet is resuspended in PBS and stored in aliquots at −80° C. Purified membranes are washed using PBS and resuspended in binding buffer (50 mM Tris(HCl), pH 7.4,5 mM KCl, 120 mM NaCl, 2 mM $CaCl_2$, 1 mM $MgCl_2$, 0.1% bovine serum albumin (BSA)). Membranes (20 $\mu$g/reaction tube) are added to polypropylene tubes containing 0.050 nM [125I1] PYY(porcine), displacers ranging from 10–12 M to $10^{-12}$ M to $10^{-5}$ M, and buffer to yield a final volume of 0.250 mL. Nonspecific binding is determined in the presence of 1 $\mu$M NPY(human) and accounts for 10% of total binding. Following a 2 hour incubation at room temperature, the reaction is terminated by rapid vacuum filtration. Samples are filtered over presoaked GF/C Whatman filters (1.0% polyethylenemine) and rinsed 2 times with 5 mLs cold binding buffer without BSA. A gamma counter is used to count filters with a n efficiency of 85%. $IC_{50}$ values were calculated with the non-linear curve fitting program RS/1 (Sigma Plot, Jandel).

The compounds of general formula I may be administered orally, topically, parenterally, by inhalation or spray or rectally in dosage unit formulations containing conventional non-toxic pharmaceutically acceptable carriers, adjuvants and vehicles. The term parenteral as used herein includes subcutaneous injections, intravenous, intramuscular, intra sternal injection or infusion techniques. In addition, there is provided a pharmaceutical formulation comprising a compound of general formula I and a pharmaceutically acceptable carrier. One or more compounds of general formula I may be present in association with one or more non-toxic pharmaceutically acceptable carriers and/or diluents and/or adjuvants and if desired other active ingredients. The pharmaceutical compositions containing compounds of general formula I may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipient which are suitable for the manufacture of tablets. These excipient may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipient suitable for the manufacture of aqueous suspensions. Such excipients are suspending agents, for example sodium carboxymethyl cellulose, methylcellulose, hydropropylmethylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax hard paraffin. or cetyl alcohol. Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipient, for example sweetening, flavoring and coloring agents, may also be present.

Pharmaceutical compositions of the invention may also be in the form of oil-in-water emulsions. The oily phase may be a vegetable oil, for example olive oil or arachid oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono-or diglycerides. In addition, fatty acids such as oleic acid find use in the preparation of injectables.

The compounds of general formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Compounds of general formula I may be administered parenterally in a sterile medium. The drug, depending on the vehicle and concentration used, can either be suspended or dissolved in the vehicle. Advantageously, adjuvants such as local anaesthetics, preservatives and buffering agents can be dissolved in the vehicle.

Dosage levels of the order of from about 0.1 mg to about 140 mg per kilogram of body weight per day are useful in the treatment of the above indicated conditions (about 0.5 mg to about 7 g per patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient. Dosages to be used will depend upon the particular use to which the composition is to be used.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

An illustration of the preparation of compounds of the present invention is given in Scheme I. Those having skill in the art will recognize that the starting materials may be varied and additional steps employed to produce compounds encompassed by the present invention.

Scheme 1

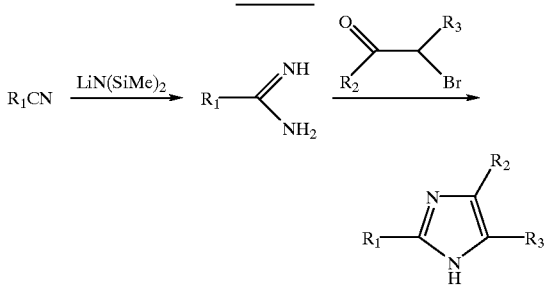

where $R_1$, $R_2$ and $R_3$ are as defined above.

The invention is illustrated further by the following examples which are not to be construed as limiting the invention in scope or spirit to the specific procedures and compounds described in them.

EXAMPLE 1

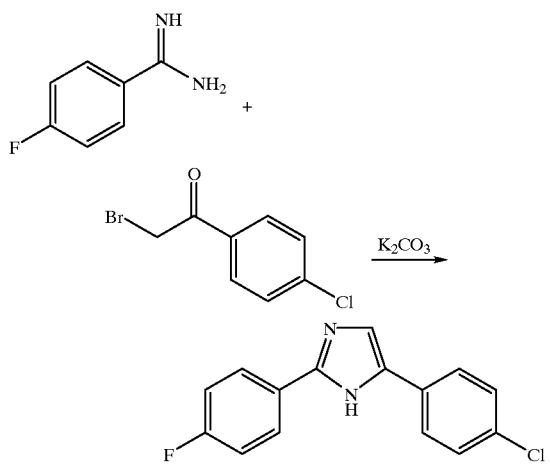

To a two-phase mixture of 30% $K_2CO_3$ solution (5 ml) and chloroform (5 mL) containing 276 mg of 4-fluorobenzamidine was added a solution of 468 mg of 2-bromo-4'-chloroacetophenone in chloroform (3 mL). After stirring for 1 hr, the reaction mixture was filtered. The white crystallinesolid was washed with distilled water and dried in a vacuum oven overnight to afford 2-(4-fluorophenyl)4-(4-chlorophenyl)imidazole (Compound 1).

EXAMPLE 2

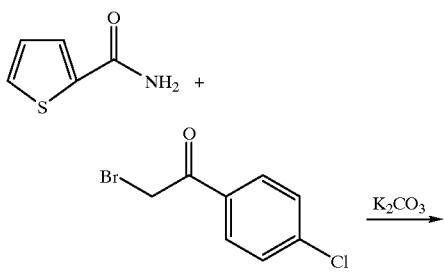

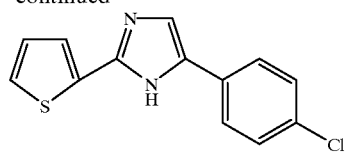

To a solution of 2-cyanothiophene (10.9 g) in anhydrous diethyl ether (200 mL) was added solid lithium bis(trimethylsilyl)amide (24 g). After 30 min the stirred reaction was cooled in ice and 2 N HCl solution was added dropwise until the mixture was acidic to pH paper. The reaction was stirred for an additional 30 min and transferred to a separator funnel. The acidic extract was separated and the ethereal layer was discarded. The acidic aqueous layer was returned to the separator funnel, basified with 10 N NaOH solution and extracted with chloroform (2×150 mL). The organic extracts were dried over—potassium carbonate, filtered and concentrated to provide the desired 2-thienyl carboxamidine (8 g) as an orange solid To a two-phase mixture of 30% $K_2CO_3$ (5 ml) and chloroform (5 mL) containing 126 mg of thiophen-2-yl carboxamidine was added a solution of 233 mg of 2-bromo4'- chloroacetophenone in 3 ml of chloroform. After stirring for 1 h, the organic layer was dried ($Na_2SO_4$) and concentrated. Purification on preparative TLC (5% MeOH/$CH_2Cl_2$) afforded 2-(2othienyl)-4-(4-chlorophenyl) imidazole (Compound 2).

EXAMPLE 3

Synthesis of Biarylimidazole acids

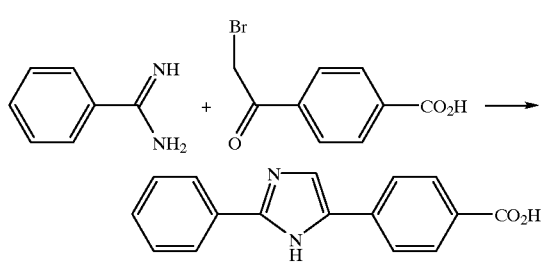

To a mixture of the bromoacid (2.00 g, 8.20 mmol, 1.0 equiv) in THF (200 mL) was added the benzamidine free base (4.92 g, 41.0 mmol 5.0 equiv) as a solid. After stirring at room temperature for 15 minutes, the mixture was evaporated, and the crude product was purified by flash chromatography (95% EtOAc, 5% MeOH) to afford the biphenylimidazole acid as a colorless solid.

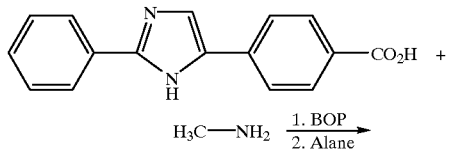

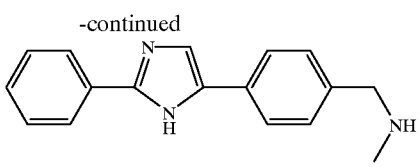

To 0.1 mL of a 0.2M solution of the acid in 95% toluene/5% N-methylmorpholine was added 0.1 mL of a solution of 0.2M methylamine in 95% toluene/5% N-methylmorpholine, followed by 0.15 mL of a 0.2M solution of benzotriazol-1-yl-oxy-tris(dimethylamino)phosphonium-hexafluorophosphate (BOP) in dichloromethane, and the mixture was stirred at room temperature for 2 h. Chromatography (1 g silica gel, EtOAc) afforded the amide as a yellow oil which was immediately reduced by adding 0.4 mL of a 0.5M alane dimethylethylamine complex in toluene. This mixture was stirred at room temperature for 2 hours, then was dissolved in ethyl acetate and washed with 1M NaOH and evaporated to provide the amine.

Particularly preferred compounds include:
4-(4-fluorophenyl)-2-phenylimidazole
2-fluoro-4-[2-(4-fluorophenyl)imidazol-4-yl]-1-methoxybenzene
4-ethoxy-2-fluoro-1-(2-phenylimidazol-4-yl)benzene
4-methoxy-3-fluoro-1-(2-phenylimidazol-4-yl)benzene
3-fluoro-4-[2-(4-fluorophenyl)imidazol-4-yl]-1-methoxybenzene
3-methoxy-1-(2-phenylimidazol-4-yl)benzene
2-methyl-1-(2-phenylimidazol-4-yl)benzene
4-[2-(4-methoxyphenyl)imidazol-4-yl]-1-chlorobenzene
4-methoxy-2-fluoro-1-(2-phenylimidazol-4-yl)benzene
4-(4-chlorophenyl)-2-phenylimidazole
4-(4-methylphenyl)-2-phenylimidazole
4-(4-methoxyphenyl)-2-phenylimidazole
4-(3-bromophenyl)-2-phenylimidazole
1-[3-(2-phenylimidazol-4-yl)phenyl]ethan-1-one
4-(4-bromophenyl)-2-phenylimidazole
4-(3-cyanophenyl)-2-phenylimidazole
4-(3-cyanophenyl)-2-(4-fluorophenyl)imidazole
4-(4-cyanophenyl)-2-phenylimidazole
N-[3-(2-phenylimidazol-4-yl)phenyl]acetamide
ethyl 2,4-diphenylimidazole-5-carboxylate
(2,4-diphenylimidazol-5-yl)methan-1-ol
2-(4-fluorophenyl)-5-methyl-4-phenylimidazole
4-[2-(2-fluorophenyl)imidazol-4-yl]-1-chlorobenzene
4-(2-naphthyl)-2-imidazole
6-(2-phenylimidazol-4-yl)-2H,3H-benzo[e]1,4dioxin
6-[(2-(4-fluoropheny)limidazol-4-yl)-2H,3H-benzo[e]1,4dioxin
6-{2-[4-trifluoromethyl)pheny]limidazol-4-yl}-2H,3H-benzo[e]1,4dioxin
6-[(2-(4-fluoropheny)-5-methylimidazol-4-yl)-2H,3H-benzo[e]1,4dioxin
6-(2-2-pyridyl)imidazol-4-yl)-2H,3H-benzo[e]1,4dioxin
6-(2-phenylimidazol-4-yl)benzo[b]morpholine
4-methyl-6-{2-phenylimidazol-4-yl)benzo[b]morpholine
4-propyl-7-{2-phenylimidazol-4-yl)benzo[b]morpholine
6-[2-(4-fluorophenylimidazol-4-yl)benzo[b]morpholine
6-[2-(4-fluorophenylimidazol-4-yl)-4-methylbenzo[b]morpholine
4-ethyl-6-[2-(4-fluorophenyl)imidazol-4-yl)benzo[b]morpholine
6-[2-(4-fluorophenylimidazol-4-yl)-2H,3H,4H-benzo[e]1,4-thiazine
4-methyl-6-[2-(4-fluorophenylimidazol-4-yl)-2H,3H,4H-benzo[e]1,4-thiazine
4-(4-chlorophenyl-2-(2-pyridyl)imidazole
2-[4-(4-chlorophenyl)imidazol-2-yl]pyrazine
4-[2-(4-fluorophenyl)imidazolyl-4-yl-chlorobenzene
2-indole-3yl-5-methyl-4-phenylimidazole
2-[4-(4-chlorophenyl)imidazol-2-yl]thiophene
4-(6-chloro(2-pyridyl)-2-phenylimidazole
dimethyl[2-(2-phenylimidazolyl-4-yl)(4-pyridyl)]amine
[3-(2-phenylimidazol-4-yl)phenyl]methylamine
{3-[2-(4-fluorophenyl)imidazol-4-yl]phenyl}methylamine
methyl[3-(2-phenylimidazol-4-yl)phenyl]methyl}amine
dimethyl[3-(2-phenylimidazol-4-yl)phenyl]methyl}amine
methyl[4-(2-phenylimidazol-4-yl)phenyl]methyl}amine
dimethyl[4-(2-phenylimidazol-4-yl)phenyl]methyl}amine
ethyl[3-(2-phenylimidazol-4-yl)phenyl]amine
({3-[2-(4-fluorophenyl)imidazol-5-yl]phenyl}methyl)(2-methylbutyl)amine
(ethylbutyl)({3-[2-(4-fluoropheyl)imidazol-5-yl]phenyl}methyl)amine
(1,2-dimethylpropyl)({3-[2-(4-fluorophenyl)imidazol-5-yl}methyl)amine
(3-cyclohexyl-1-phenylpropyl)methyl{[3-(2-phenylimidazol-5-yl)phenyl]methyl}amine
({3-[2-(4-fluorophenyl)imidazol-5-yl]phenyl}methyl)methylbutyl)amine
(2-methylbutyl){[3-(2-phenylimidazol-5-yl)phenyl]methyl}amine
(2-cyclohex-1-enylethyl)({3-[2-(4-fluorophenyl)imidazol-5-yl]phenyl}methyl)amine
(cyclohexylphenylmethyl)methyl{[3-[2-phenylimidazol-5-yl)phenyl]methyl}amine
ethyl(1-{3-[2-(4-fluorophenyl)imidazol-5-yl]-isopropyl)amine
({3-[2-(4-fluorophenyl)imidazol-5-yl]phenyl}methyl)[3-methylethoxy)propyl]amine
(tert-butyl)({3-[2-(4-fluorophenyl)imidazol-5-yl]phenyl}methyl)amine
methyl{phenyl[3-(2-phenylimidazol-5-yl)phenyl]methyl}propylamine
(tert-butyl) {[3-(2-phenylimidazol-5-yl)phenyl]methyl}amine
(methylethyl) {[3-(2-phenylimidazol-5-yl)phenyl]methyl}amine
({3-[2-(4-fluorophenyl)imidazol-5-yl]phenyl}methyl)[(4-methylphenyl)methyl]amine
(cyclohexylphenylmethyl)({3-[2-(4-fluorophenyl)imidazole-5-yl]phenyl}methyl)methylamine
cyclopentyl {[3-(2-phenylimidazol-5-yl)phenyl]methyl}amine
(methylpropyl){[3-(2-phenylimidazol-5-yl)phenyl]methyl}amine
({3-[2-(4-fluorophenyl)imidazol-5-yl]phenyl}methyl)(2-methylpropyl)amine
({3-[2-(4-fluorophenyl)imidazol-5-yl]phenyl}methyl)pentylamine
({3-[2-(4-fluorophenyl)imidazol-5-yl]phenyl}methyl)(methylethyl)amine
cyclopropyl({3-[2-(4-fluorophenyl)imidazol-5-yl]phenyl}methyl)amine cyclobutyl({3-[2-(4-fluorophenyl)imidazol-5-yl]phenyl}methyl)amine
({3-[2-(4-fluorophenyl)imidazol-5-yl ]phenyl}methyl)[2-(4-methylphenyl)ethyl]amine
hexyl{[3-(2- phenylimidazol-5-yl)phenyl]methyl}amine
(methylbutyl) {[3-(2-phenylimidazol-5-yl)phenyl]methyl}amine
({3-[2-(4-fluorophenyl)imidazol-5-yl]phenyl}methyl)hexylamine
(1,1-dimethylpropyl) {[3-(2-phenylimidazol-5-yl)phenyl]methyl}amine)

({3-[2-(4-fluorophenyl){[3-(2-phenylimidazol-5-yl)phenyl] methyl}amine
(2-cyclohexyl-1-phenylethyl)methyl{[3-(2-phenylimidazol-5-yl)phenyl]methyl}amine
{[3-(2-phenylimidazol-5-yl)phenyl]methyl}propylamine
({3-[2-(4-fluorophenyl)imidazol-5-yl]phenyl}methyl)(2-phenylethyl)amine
(2-cyclopentyl-1-phenylethyl)methyl{[3-(2-phenylimidazol-5-yl)phenyl]methyl}amine
(2-cyclohex-1-enylethyl){[3-(2-phenylimidazol-5-yl)phenyl]methyl}amine
({3-[2-(4-fluorophenyl)imidazol-5-yl]phenyl}methyl)benzylamine
(ethylpropyl){[3-(2-phenylimidazol-5-yl)phenyl]methyl}amine
cyclobutyl{[3-(2-phenylimidazol-5-yl)phenyl]methyl}amine
(3-methylbutyl){[3-(2-phenylimidazol-5-yl)phenyl]methyl}amine
[2-(4-methylphenyl)ethyl]{[3-(2-phenylimidazol-5-yl)phenyl]methyl}amine
(3-cyclohexyl-1-phenylpropyl)({3-[2-(4-fluorophenyl)imidazol-5-yl]phenyl}methyl)methylamine
cyclopropyl{[3-(2-phenylimidazol-5-yl)phenyl]methyl}amine
(1,2-dimethylpropyl){[3-(2-phenylimidazol-5-yl)phenyl]methyl}amine
ethyl({3-[2-(4-fluorophenyl)midazol-5-yl]phenyl}methyl)amine
({3-[2-(4-fluorophenyl)imidazol-5-yl]phenyl}methyl)(3-methylbutyl)amine
ethyl{[3-(2-phenylimidazol-5-yl)phenyl]methyl}amine
cyclohexyl({3-[2-(4-fluorophenyl)imidazol-5-yl]phenyl}methyl)amine
methyl{[3-(2-phenylimidazol-5-yl)phenyl]methyl}amine
pentyl{[3-(2-phenylimidazol-5-yl)phenyl]methyl}amine
([3-[2-(4-fluorophenyl)imidazol-5-yl]phenyl}methyl)dipropylamine
dibutyl[3-(2-phenylimidazol-5-yl)phenyl]methyl}amine.

Such compounds have $IC_{50}$ values between 1 nM and 1 μM.

With the exception of 4-(4-methylphenyl)-2-phenylimidazole 4-(2-methylphenyl)-2-phenylimidazole, 4-(4-chlorophenyl)-2-phenylimidazole and 4-(4-bromophenyl)-2-phenylimidazole, all of the preferred compounds listed above are believed to be novel.

The activities of compounds according to the invention have been investigated in the above mentioned tests.

Food Deprivation Protocol

Subjects. Experimentally naive and experienced male Sprague Dawley rats (Sasco, St. Louis, Mo.) weighing between 210 and 310 g at the beginning of the experiment are employed. The animals are housed in a temperature-controlled (22° C.12° ) and humidity-controlled (40–70%RH) animal facility with a 12 h light: 12 h dark lighting schedule. The lights are on from 0530 till 1730 daily. When not in the experimental protocol animals are allowed free access to food (Standard Rat Chow, PMI Feeds Inc., #5012) and water. Animals are housed in stainless steel hanging home cages in groups of two while not in the experimental protocol. For data collection, the animals are transferred to individual plastic metabolic cages located in the same room.

Apparatus. Consumption and elimination data are collected data are collected while the animals are housed in Nalgene Metabolic Cages (Model #650-010). Each cage is comprised of subassemblies of clear polymethylpentene (PMP), polycarbonate (PC), and stainless steel (SS). All parts disassemble for quick and accurate data collection and for cleaning.

The entire cylinder-shaped plastic and stainless steel cages rests on a stainless steel stand and houses one animal. The animal is contained in the round Upper Chamber (PC) assembly (12 cm high and 20 cm in diameter) and rests on a stainless steel floor (20 cm diameter). Two subassemblies are attached to the Upper Chamber. The first subassembly consists of a 5.5. feeding chamber (10 cm long, 5 cm high and 5 cm wide) with a PC feeding draw attached to the bottom. The feeding drawer has two compartments: A food storage compartment with a capacity for approximately 50 grams of pulverized rat chow and a food spillage compartment. The food storage compartment is distal to the Upper Chamber while the spillage compartment is proximal to the Upper Chamber. The animal is allowed access to the pulverized chow by an opening in the 55 floor of the feeding chamber. The floor of the feeding chamber does not allow access to the food dropped into the spillage compartment.

The second subassembly adjacent to the Upper Chamber includes a water bottle support, a P.C. water bottle (100 ml capacity) and a graduated water spillage collection tube. The water bottle support funnels any spilled water into the water spillage collection tube.

The lower chamber consists of a PMP Separating Cone, PMP collection funnel, PMP fluid (urine) collection tube (70 ml capacity), and feces collection tube. The Separating Cone is attached to the top of the collection funnel which is attached to the bottom of the Upper Chamber. The urine runs off the Separating Cone onto the walls of the collection funnel and into the urine collection tub. The Separating Cone also separates the feces and funnels it into the feces Collection tube.

A Ohaus portable Advanced Scale (I 0.1 g accuracy) is used to weigh the rats, food and water contains, and the urine and feces collection tubes.

Procedure. The effects of the experimental compound on body weight, food and water consumption, and fecal and urinary excretion are assessed using the Metabolic Cages. Rats are weighed prior to the assignment to experimental groups. Assignment is made using a quasirandom method utilizing pre-assignment body weights to assure that the treatment groups had similar average body weight.

All food is removed from the home cage the night before testing. On the test day, approximately 1 hour prior to dosing, the animals are weighed tot he nearest 0.5 g. For oral drug administration the animals are dosed with either methyl cellulose (MC) or one does of experimental compound and returned to their home cage. For intravenous (IV) dosing, the animals are dosed with either PEG400 or one dose of experimental compound. After the appropriate pretreat time each animal is placed into a Metabolic Cage for a 1 hour test session. Prior to testing, the feeding drawer filled water bottle, are weighed. In addition, the empty feces and urine collection tubes are weighed Following the test session, the rats are removed from the metabolic cages, weighted, and returned to their home cages. The food and water containers, as well as the feces and urine collection tubes, are then weighed and recorded.

Drugs. For oral dosing experiments, the experimental compound is suspended in 0.5% methyl cellulose (MC). Experimental compound or MC is administered orally (PO) in a dosing volume of 10 ml/kg. Drug is made into a homogenous suspension by stirring and ultrasonication. The drug or vehicle suspension is administered 45–60 min prior to test via 6 cm piece of polyethylene (PE 90) tubing attached via a Leur lock hub to a 5 cc Becton Dickson syringe. For intravenous (IV) dosing, the experimental compound is dissolved in a 50% polyethylene glycol (PEG)-400, 50% distilled water solution. The animals are dosed with either PEG400 (1 to 4 m]/kg) or one dose of experimental compound (1 to 4 ml/kg) 5 min prior to test.

Statistical Analyses. The means and standard areas of the mean (SEM) for body weight, food consumption, water consumption, fecal excretion, and urinary excretion are presented. One way analysis of variance (ANOVA) is carried out using the Macintosh version of Systat (version 5.2.1). Post-hoc analysis is conducted using the Fisher LSD test. A significant effect is defined as having a p value of <0.05.

The following parameters are defined: Body weight gain is the difference between the body weight of the animal at the time of dosing and the body weight of the animal following dosing. Food consumption is the difference in the weight of the food drawer between dosing and post testing. Water consumption is the difference in the weight of the water bottle between dosing and post testing.

Fecal excretion is the difference in the weight of the empty fecal collection tube and the weight of the tube post testing. Urinary excretion is the difference in the weight of the empty urinary collection tube and the weight of the tube post testing.

What is claimed is:

1. A method of treating conditions susceptible to modulation of NPY receptors which comprises administering to a patient suffering from such conditions an effective dose of a compound of the formula:

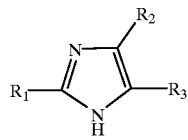

or a pharmaceutically acceptable salt
where $R_1$ is an unsubstituted or mono, di or trisubstituted aryl group wherein said aryl group is mono or bicyclic, in which case only the ring bound to the imidazole ring must be aromatic, and said aryl group is carbocyclic or contain up to 2 hetero atoms selected from the group consisting of nitrogen, oxygen and sulfur and said substituents are individually selected from the group consisting of halogen, trihalomethyl, cyano, hydroxy, straight or branched chain lower alkyl having 1–6 carbon atoms, straight or branched chain lower alkoxy having 1–6 carbon atoms (which alkyl or alkoxy groups themselves are unsubstituted or substituted by an amino or a mono- or di-alkyl amino group or by a mono- or di-alkarylamino group or by an acyl group), straight or branched chain lower thioalkoxy having 1–6 carbon atoms, acyloxy groups, amino, amino mono or disubstituted with straight or branched chain lower alkyl having 1–6 carbon atoms, said alkyl groups being unsubstituted or substituted with a hydroxy or amino group, alkyl, aryl or alkaryl amide groups the nitrogen atom of which is bound to the aryl group, mono or disubstituted carbamyl wherein the CO group is bound to the aryl group and wherein each substituent is lower alkyl or aryl lower alkyl, mono or di-alkyl carbamates having up to 6 carbon atoms in each alkyl group or mono or diaryl carbamates or any 2 adjacent substituents bound to the aryl group form a group of the formula —X—$(CH_2)_n$—Y—$(CH_2)_m$—Z— where X, Y and Z are either a direct bond, oxygen, sulfur, or NR where R is hydrogen or lower alkyl and n and m are 1, 2 or 3;

one of $R_2$ and $R_3$ is selected from the group consisting of hydrogen, hydroxymethyl, alkoxymethyl having up to 6 carbon atoms in each alkoxy group, straight or branched chain lower alkyl having 1–6 carbon atoms, cyano, or a carboxylic or carboxylate ester group wherein the esterifying group contains up to six carbon atoms;

the other of $R_2$ and $R_3$ is an aryl group which is either unsubstituted or mono, di or trisubstituted wherein said aryl groups are mono or bicyclic (in which case only the ring bound to the imidazole ring need be aromatic) and may be carbocyclic or contain up to 2 hetero atoms and said substituents are individually selected from the group consisting of halogen, trihalomethyl, cyano, hydroxy, straight or branched chain lower alkoxy having 1–6 carbon atoms, straight or branched chain lower alkoxy having 1–6 carbon atoms (which alkyl and alkoxy groups themselves are unsubstituted or substituted by an amino group, or a mono- or di-alkylamino group, a nitrogen-containing ring, a mono- or di-alkaryl group or by an acyl group or a carbamate), straight or branched chain lower thioalkoxy having 1–6 carbon atoms, acyloxy groups, amino, amino mono or disubstituted with straight or branched chain lower alkyl having 1–6 carbon atoms (said alkyl groups being unsaturated or substituted with a hydroxy or amino group), alkyl, aryl and alkaryl amide groups the nitrogen atom of which is bound to the aryl group, mono or disubstituted carbamyl wherein the CO group is bound to the aryl group and wherein each substituent is lower alkyl or aryl lower alkyl, mono- or di-alkyl carbamates having up to 6 carbon atoms in each alkyl group or mono or diaryl carbamates additionally any two adjacent substituents of the aryl group may be represented as —X—$(CH_2)_n$—Y—$(CH_2)_m$—Z— where X, Y and Z are either a direct bond, oxygen, sulfur, or NR where R is hydrogen or lower alkyl and n and m are 1,2 or 3.

2. A method as claimed in claim 1, wherein said compound is one wherein each aryl group is selected independently from the group consisting of unsubstituted or substituted phenyl, naphthyl, indanyl, pyrrolyl, furanyl, thienyl, pyridyl, pyrimidinyl, indolyl, benzofuranyl, thianaphthyl, isoindolyl, isobenzofuranyl, quinolinyl, isoquinolinyl, quinazolinyl, indazolyl, quinoxalinyl, cinnolinyl 1,2,3,4-tetrahydroquinolinyl, 2,3-dihydroindolyl, phenomorpholinyl, benzodioxazinyl, phenothiomorpholinyl and methylenedioxyphenyl groups.

3. A method as claimed in claim 1, wherein said compound is one wherein $R_1$ is a a substituted or unsubstituted phenyl or naphthyl group.

4. A method according to claim 1, wherein the compound is one wherein $R_1$ is phenyl or 4-fluorophenyl.

5. A method according to claim 1, wherein one of $R_2$ and $R_3$ is hydrogen or methyl and the other is selected from the group consisting of 4-methylphenyl, 3-methoxyphenyl, 4-methoxyphenyl, 3-bromophenyl, 4-bromophenyl, 4-chlorophenyl, 4-fluorophenyl, 3-cyanophenyl, 4-cyanophenyl, 4-methoxy-2-fluorophenyl, 4-ethoxy-2-fluorophenyl, 3-fluoro-4-methoxyphenyl, 2-fluoro-4-methoxyphenyl, 3-acetylphenyl, naphthyl, 1,4-benzodioxan-6-yl and benzo [b] morpholinyl, 4-alkyl benzo [b] morpholinyl and 4-alkyl.-2H,3H,4H-benzo[e]1,4-thiazinyl.

6. A method according to claim 1, wherein one of $R_2$ or $R_3$ is hydrogen or methyl and the other is selected from the group consisting of 3-methylaminophenyl 4-dimethylaminophenyl, 3-ethylaminophenyl, 3-(2-methylbutylaminomethyl)phenyl, 3-(ethylbutylaminomethyl)phenyl, 3-(1,2-dimethylpropylaminomethyl)phenyl, 3-[(3-cyclohexyl-1-phenylpropyl)methylaminomethyl]phenyl, 3-[(2-cyclohex-1-enylethyl)aminomethyl]phenyl, 3-[(3-methylethoxy)propylaminomethyl]phenyl,. 3-(tert.-butylaminomethyl)phenyl, 3-[methyl-(1-phenylpropyl)aminomethyl]phenyl, 3-(methylethylaminomethyl)phenyl and 3-[(4-methylphenyl)metylaminomethyl]phenyl.

7. A method according to claim 1, wherein the compound administered is selected from the group consisting of 4-(4-fluorophenyl)-2-phenylimidazole
2-fluoro-4-[2-(4-fluorophenyl)imidazol-4-yl]-1-methoxybenzene
4-ethoxy-2-fluoro-1-(2-phenylimidazol-4-yl)benzene
4-methoxy-3-fluoro-1-(2-phenylimidazol-4-yl)benzene
3-fluoro-4-[2-(4-fluorophenyl)imidazol-4-yl]-1-methoxybenzene
3-methoxy-1-(2-phenylimidazol-4-yl)benzene
4-[2-(4-methoxyphenyl)imidazol-4-yl]-1-chlorobenzene
4-methoxy-2-fluoro-1-(2-phenylimidazol-4-yl)benzene
4-(4-chlorophenyl)-2-phenylimidazole
4-(4-methylphenyl)-2-phenylimidazole
4-(4-methoxyphenyl)-2-phenylimidazole
4-(3-bromophenyl)-2-phenylimidazole
1-[3-(2-phenylimidazol-4-yl)phenyl]ethan-1-one
4-(4-bromophenyl)-2-phenylimidazole
4-(3-cyanophenyl)-2-phenylimidazole
4-(3-cyanophenyl)-2-(4-fluorophenyl)imidazole
4-(4-cyanophenyl)-2-phenylimidazole
N-[3-(2-phenylimidazol-4-yl)phenyl]acetamide
2-(4-fluorophenyl)-5-methyl-4-phenylimidazole
4-[2-(2-fluorophenyl)imidazol-4-yl]-1-chlorobenzene
4-(2-naphthyl)-2-imidazole
6-(2-phenylimidazol-4-yl)-2H,3H-benzo[e]1,4dioxin
6-[(2-(4-fluoropheny)limidazol-4-yl)-2H,3H-benzo[e]1,4dioxin
6-[(2-(4-fluoropheny)-5-methylimidazol-4-yl)-2H,3H-benzo[e]1,4dioxin
6-(2-phenylimidazol-4-yl)benzo[b]morpholine
4-methyl-6-{2-phenylimidazol-4-yl)benzo[b]morpholine
4-propyl-7-{2-phenylimidazol-4-yl)benzo[b]morpholine
6-[2-(4-fluorophenylimidazol-4-yl)benzo[b]morpholine
6-[2-(4-fluorophenylimidazol-4-yl)-4-methylbenzo[b]morpholine
4-ethyl-6-[2-(4-fluorophenyl)imidazol-4-yl)benzo[b]morpholine
4-methyl-6-[2-(4-fluorophenylimidazol-4-yl)-2H,3H,4H-benzo[e]1,4-thiazine
4-(4-chlorophenyl-2-(2-pyridyl)imidazole
4-[2-(4-fluorophenyl)imidazol-4-yl-chlorobenzene
2-indole-3yl-5-methyl-4-phenylimidazole
2-[4-(4-chlorophenyl)imidazol-2-yl]thiophene
[3-(2-phenylimidazol-4-yl)phenyl]methylamine
dimethyl[3-(2-phenylimidazol-4-yl)phenyl]methyl}amine
dimethyl[4-(2-phenylimidazol-4-yl)phenyl]methyl}amine
ethyl[3-(2-phenylimidazol-4-yl)phenyl]amine
({3-[2-(4-fluorophenyl)imidazol-5-yl]phenyl}methyl)(2-methylbutyl)amine
(ethylbutyl)({3-[2-(4-fluorophenyl)imidazol-5-yl]phenyl}methyl)amine
(1,2-dimethylpropyl)({3-[2-(4-fluorophenyl)imidazol-5-yl}methyl)amine
(3-cyclohexyl-1-phenylpropyl)methyl{[3-(2-phenylimidazol-5-yl)phenyl]methyl}amine
({3-[2-(4-fluorophenyl)imidazol-5-yl]phenyl}methyl) methylbutyl)amine
(2-methylbutyl){[3-(2-phenylimidazol-5-yl)phenyl]methyl}amine
(2-cyclohex-1-enylethyl)({3-[2-(4-fluorophenyl)imidazol-5-yl]phenyl}methyl)amine
(cyclohexylphenylmethyl)methyl{[3-[2-phenylimidazol-5-yl)phenyl]methyl}amine
ethyl(1-{3-[2-(4-fluorophenyl)imidazol-5-yl}-isopropyl)amine
({3-[2-(4-fluorophenyl)imidazol-5-yl]phenyl}methyl)[3-methylethoxy)propyl]amine
(tert-butyl)({3-[2-(4-fluorophenyl)imidazol-5-yl]phenyl}methyl)amine
methyl{phenyl[3-(2-phenylimidazol-5-yl)phenyl]methyl}propylamine
(tert-butyl){[3-(2-phenylimidazol-5-yl)phenyl]methyl}amine
(methylethyl){[3-(2-phenylimidazol-5-yl)phenyl]methyl}amine
({3-[2-(4-fluorophenyl)imidazol-5-yl]phenyl}methyl)[(4-methylpheny)methyl]amine.

8. A method as claimed in claim 1, wherein the receptor is an NPY5 receptor.

9. A method as claimed in claim 1, wherein $R_1$ is a pyridin-2-yl or a 2- or 3-thienyl group.

10. A method as claimed in claim 1, wherein the non-aryl $R_2$ or $R_3$ group is selected from hydrogen and, alkyl.

11. A method as claimed in claim 1, wherein whichever of $R_2$ and $R_3$ is aryl is selected from the group consisting of a substituted or unsubstituted aryl group selected from the groups consisting of phenyl, 2- or 3-thienyl, 1,4 benzodioxan-6-yl, benzo[b]morpholinyl , and naphthyl and wherein if substituted said aryl group is substituted by up to three substituents selected from halo, cyano, alkoxy and alkyl groups.

12. A method as claimed in claim 11, wherein said aryl group bears one or two substituents selected from the group consisting of alkyl of 1–6 carbon atoms, fluoro, chloro, bromo, cyano and alkoxy of 1 to 6 carbon atoms.

13. A method as claimed in claim 11, wherein said aryl group bears an N-substituted aminomethyl substituent.

14. A method as claimed in claim 3, wherein whichever of $R_2$ and $R_3$ is aryl is a substituted or unsubstituted aryl group selected from the group consisting of phenyl, 2- or 3-thienyl, 1,4 benzodioxan-6-yl, benzo[b]morpholinyl, and naphthyl and when it is substituted, said aryl group is substituted by up to three substituents selected from halo, cano, alkoxy and alkyl groups.

15. A method as claimed in claim 14, wherein said aryl group bears one or two substituents selected from the group consisting of alkyl of 1–6 carbon atoms, fluoro, chloro, bromo, cyano and alkoxy of 1 to 6 carbon atoms.

16. A method as claimed in claim 14, wherein said aryl group bears an N-substituted aminomethyl substituent.

17. A method as claimed in claim 14, wherein $R_2$ or $R_3$ is selected from the group consisting of 4-methylphenyl, 3-methoxyphenyl, 4- methoxyphenyl, 3-bromophenyl, 4-bromophenyl, 4-chlorophenyl, 4-fluorophenyl, 3-cyanophenyl, 4-cyanophenyl, 4-methoxy-2-fluorophenyl, 4-ethoxy-2-fluorophenyl, 3-fluoro-4-methoxyphenyl, 2-fluoro-4-methoxyphenyl, 3-acetylphenyl, naphthyl, 1,4-benzodioxan-6-yl and benzo [b] morpholinyl, 4-alkyl benzo [b]morpholinyl and 4-alkyl-2H,3H,4H-benzo[e]1,4-thiazinyl.

18. A method as claimed in claim 14, wherein $R_2$ or $R_3$ is selected from the group consisting of 3-methylaminophenyl, 4-dimethylaminophenyl, 3-ethylaminophenyl, 3-(2-methylbutylaminomethyl)phenyl, 3-(ethylbutylaminomethyl)phenyl, 3-(1,2-dimethylpropylaminomethyl)phenyl, 3-[(3-cyclohexyl-1-phenylpropyl)methylaminomethyl]phenyl, 3-[(2-cyclohex-1-enylethyl)aminomethy]lphenyl, 3-[(3-methylethoxy)propylaminomethyl]phenyl, 3-(tert.-butylaminomethyl)phenyl, 3-[methyl-(1-phenylpropyl)aminomethyl]phenyl, 3-(methylethylaminomethyl)phenyl and 3-[(4-methylphenyl)metylaminomethyl]phenyl.

19. A method as claimed in claim 1, wherein said compound is 2-(4-fluorophenyl)-4-(4-methoxyphenyl)imidazole hydrochloride.

20. A method as claimed in claim 1, wherein said compound is 2-(2-thien-2-yl)-4-(4-chlorophenyl)imidazole.

21. A method as claimed in claim 1, wherein said compound is 2-(4-fluorophenyl)-4-(4-chlorophenyl)imidazole hydrochloride.

22. A method as claimed in claim 1, wherein said compound is 2-phenyl-4-(3-fluoro-4-methoxyphenyl)imidazole hydrochloride.

23. A method as claimed in claim 1, wherein said condition is a feeding disorder.

24. A method as claimed in claim 2, wherein said condition is a feeding disorder.

25. A method as claimed in claim 3, wherein said condition is a feeding disorder.

26. A method as claimed in claim 4, wherein said condition is a feeding disorder.

27. A method as claimed in claim 5, wherein said condition is a feeding disorder.

28. A method as claimed in claim 6, wherein said condition is a feeding disorder.

29. A method as claimed in claim 7, wherein said condition is a feeding disorder.

30. A method as claimed in claim 9, wherein said condition is a feeding disorder.

31. A method as claimed in claim 10, wherein said condition is a feeding disorder.

32. A method as claimed in claim 11, wherein said condition is a feeding disorder.

33. A method as claimed in claim 12, wherein said condition is a feeding disorder.

34. A method as claimed in claim 13, wherein said condition is a feeding disorder.

35. A method as claimed in claim 14, wherein said condition is a feeding disorder.

36. A method as claimed in claim 15, wherein said condition is a feeding disorder.

37. A method as claimed in claim 16, wherein said condition is a feeding disorder.

38. A method as claimed in claim 17, wherein said condition is a feeding disorder.

39. A method as claimed in claim 18, wherein said condition is a feeding disorder.

40. A method as claimed in claim 19, wherein said condition is a feeding disorder.

41. A method as claimed in claim 20, wherein said condition is a feeding disorder.

42. A method as claimed in claim 21, wherein said condition is a feeding disorder.

43. A method as claimed in claim 22, wherein said condition is a feeding disorder.

* * * * *

UNITED STATES PATENT AND TRADEMARK OFFICE
CERTIFICATE OF CORRECTION

PATENT NO. : 6,121,260
DATED : September 19, 2000
INVENTOR(S) : Andrew Thurkauf, et al.

It is certified that error appears in the above-indentified patent and that said Letters Patent is hereby corrected as shown below:

On title page, item 75, "Elliot" should read - - Elliott - -.

Signed and Sealed this

Seventeenth Day of April, 2001

Attest:

NICHOLAS P. GODICI

Attesting Officer

Acting Director of the United States Patent and Trademark Office